United States Patent [19]

Lingua

[11] Patent Number: 4,519,392
[45] Date of Patent: May 28, 1985

[54] HEMOSTASING MUSCLE CLIPS FOR NEEDLELESS SURGERY

[76] Inventor: Robert W. Lingua, 3246 Alabama St., La Crescenta, Calif. 91412

[21] Appl. No.: 433,800

[22] Filed: Oct. 12, 1982

[51] Int. Cl.³ .............................................. A61B 17/12
[52] U.S. Cl. ..................................... 128/325; 128/346
[58] Field of Search ................................. 128/325, 346

[56] References Cited

U.S. PATENT DOCUMENTS

| | | | |
|---|---|---|---|
| 3,106,919 | 10/1963 | Churchville | 128/346 |
| 3,247,852 | 4/1966 | Schneider | 128/325 X |
| 3,326,216 | 6/1967 | Wood | 128/325 |
| 3,363,628 | 1/1968 | Wood | 128/325 |
| 3,766,926 | 10/1973 | Bliss | 128/325 X |
| 3,911,926 | 10/1975 | Peters | 128/325 |
| 4,016,883 | 4/1977 | Wright | 128/325 |
| 4,418,694 | 12/1983 | Beroff et al. | 128/346 X |

FOREIGN PATENT DOCUMENTS

| | | | |
|---|---|---|---|
| 2525650 | 12/1976 | Fed. Rep. of Germany | 128/346 |
| 725663 | 4/1980 | U.S.S.R. | 128/346 |

Primary Examiner—Michael H. Thaler
Attorney, Agent, or Firm—Blakely, Sokoloff, Taylor & Zafman

[57] ABSTRACT

A muscle clip comprising two opposing toothed jaws, a hinge connecting said jaws and an open end with a locking means is described. A combination of two hemostasing muscle clips connected by suture material is described for use in strabismus surgery eliminating the need for suture and needle. The muscle clip system can be used to either weaken or strengthen an extra ocular muscle.

16 Claims, 11 Drawing Figures (a)
(b)

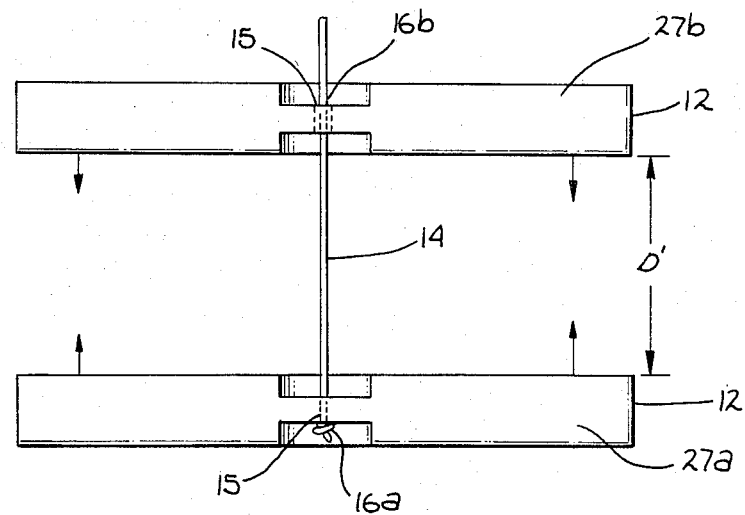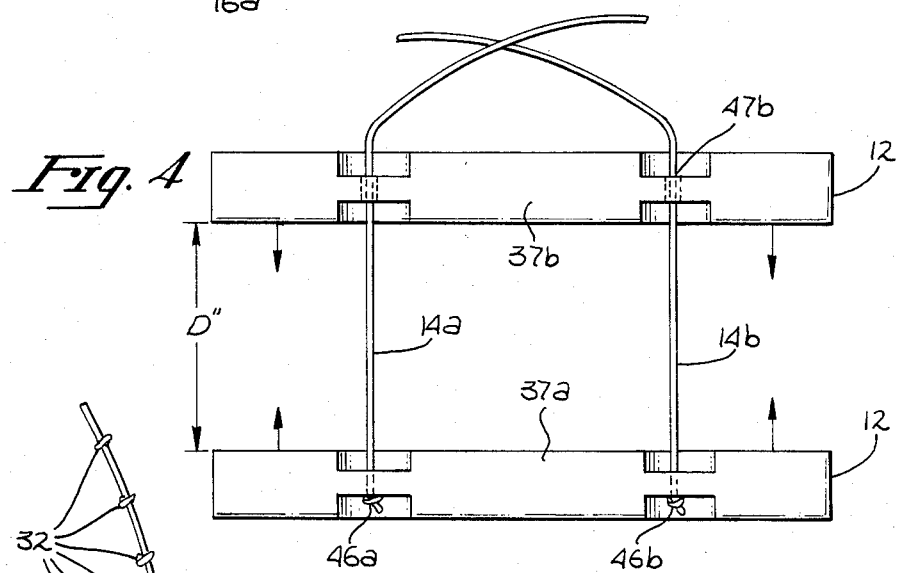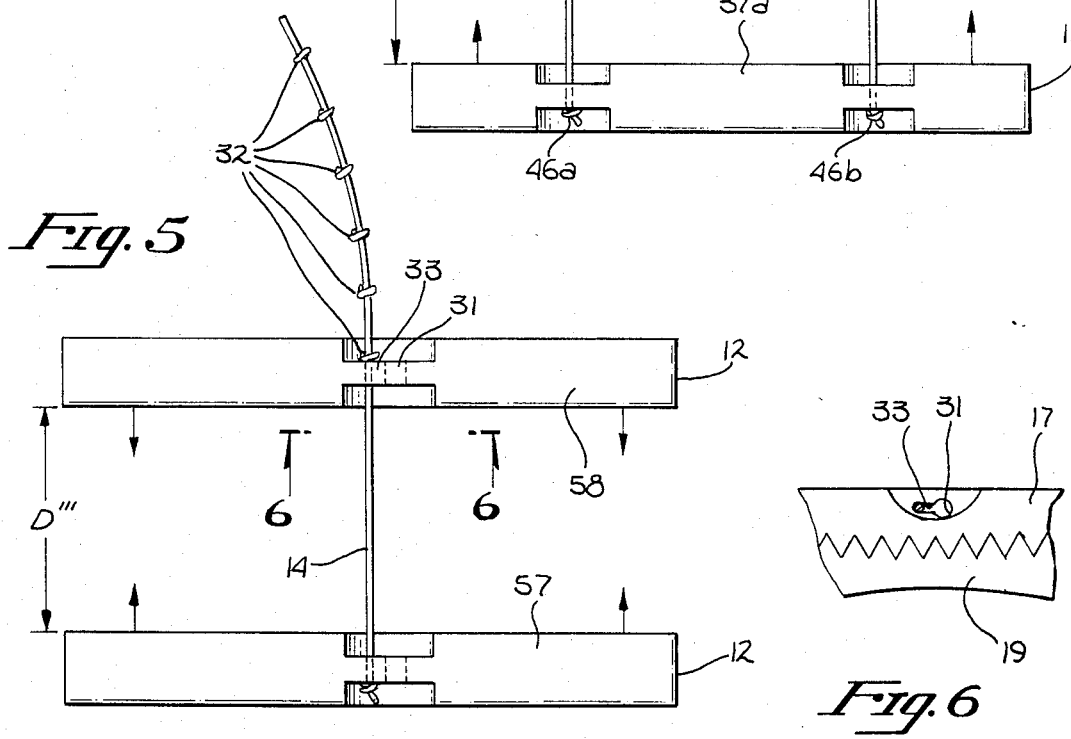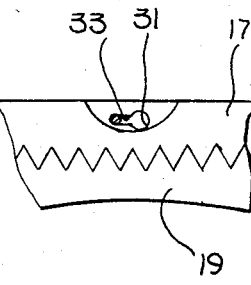

HEMOSTASING MUSCLE CLIPS FOR NEEDLELESS SURGERY

BACKGROUND OF THE INVENTION

This invention relates generally to muscle clips and the method for using the same for muscle surgery. More specifically, this invention relates to the method and apparatus for an absorbable, hemostasing, extra ocular muscle clip for needleless strabismus surgery. The purpose of this invention is to replace traditional sutures for eye muscle operations with a clip device, which because it does not require needles, avoids the serious potential complications involved with this type of procedure. The apparatus which is taught herein also solves the problem of hemorrhage during the operation which occurs because of the extensive vascularization in this area. By cross-clipping the muscles, the blood vessels are occluded, avoiding the problem of hemorrhage.

There are two major types of strabismus surgery. In one, the eye muscle is strengthened by excising a portion of the muscle and reconnecting the remaining portions. In the other type, the eye muscle is weakened by posteriorly displacing the muscle. This is done by detaching the muscle from the eye and resecuring it further back by means of suture. Both types of surgery require the use of cutting devices and needles to be used in and near the eye.

In the old method of performing strabismus surgery, the muscle is identified and elevated with a muscle hook. A suture is then weaved in and out of the muscle end with a very fine needle which may pass too superficially and miss the main structure, may pass too deeply and penetrate the eyeball or may engage one of the major blood vessles causing hemorrhage. The muscle is then cut off the eye and resecured more posterially by suture. This is accomplished by passing the needle through the tough coat of the eye (which is only 0.6 to 1.0 mm thick) and by knotting the suture in the eye and the suture in the muscle together. Serious complications may occur if penetration is either too deep or too shallow. The risks under the old technique include blindness due to penetration of the eye, hemorrhage and excessive scarring, and tremendous variability of surgical results because the surgery, at present, is done freehand; that is, in many cases without measuring the exact distance by which the eye muscle is displaced.

SUMMARY OF THE INVENTION

This invention consists of toothed or serrated locking jaws forming a clip made of an absorbable synthetic material (i.e., polydioxanone), silicone or other inert plastic. Both of the two main procedures of strabismus surgery, that of strengthening by resecting a piece of the muscle and reapproximating the two ends and of weakening a muscle action by removing it from its insertion and moving it back along the eye to a new insertion more posteriorly located may be accomplished using the apparatus and procedures described herein. A clip hinged at one end and equipped with a locking device at the other end is described hereinbelow. The bottom of the clip facing the eye is to be flat or concave with a radius of curvature of about 12 mm to conform to the curvature of the eye without causing indentation. It is to be thin enough to avoid being uncomfortable or produce an unsightly lump. The jaws of the clip are equipped with teeth, serrations or any interlocking design such that a tight grasp of the muscle is accomplished. This tight grasp will also occlude the blood vessels contained in the area, such that hemorrhaging will be prevented.

In one embodiment of this invention the muscle clips are equipped with a premeasured amount of suture between them, said suture being affixed to each clip. This embodiment is effective for quickly and accurately weakening the muscle action. One muscle clip is applied across and perpendicular to the long axis of the muscle and the other muscle clip applied approximately and adjacent to the first clip. Said clips are connected to each other by a suture of predetermined length, selected for the desired amount of recession. The clips may be conveniently applied using a forceps or clamp type tool. The muscle between the applied clips is then cut using scissors and the muscle is allowed to relax to a new more posterior position. The muscle then attaches to the eye over about a two week period due to a fibrous reaction or by use of a tissue adhesive.

In another embodiment of this invention the suture may be equipped with knots or swellings at regular intervals along the suture. The suture will be attached to one of the clips securely and pass through a hole in the other clip such that it may be easily be pulled through the hole in said clip but can be conveniently locked in a selected position by sliding the knot to a narrowed portion of the hole through which it cannot pass. The knots or swellings may be color coded or otherwise marked so that the surgeon may visually measure the amount of relaxation permitted.

To perform the surgery wherein the muscle is strengthened the following configuration of the present invention may be used. A desired amount of resection is marked off by attaching the clips at pre-determined points perpendicular to the long axis of the muscle and thereby delimiting the amount of muscle to be resected. The suture is affixed to the posterior clip and extends through slots or holes on the anterior clip. The muscle between the clips is then removed using scissors or other means and the suture material is pulled tightly through anterior clip until the posterior clip approximates the anterior clip. The suture is then tied off and the ends of the remaining muscle held by the two clips allowed to grow together.

In the above-described embodiments, a single clip, approximately 6 mm to 8 mm in length, is sufficiently long to clip off the entire muscle thereby completely occluding the blood vessels in the area in a single application. In another embodiment of the present invention, clips 3 mm to 4 mm in length are used instead of 6 mm to 8 mm clips such that two clips are applied to the muscle from opposite ends and perpendicular to the long axis of said muscle with the locking means of said clips adjacent to each other. This embodiment allows for greater security of the clip attachment to the muscle in that greater thickness in one cross-section of the muscle will not prevent the rest of the clip from tightly grasping the rest of the muscle. This is especially true where the muscle is of irregular thickness along its cross-section, due to prior surgical or disease induced scarring so that a single 6 mm to 8 mm clip may be tightly grabbing the muscle in the middle yet be too loose at the less thick sections to adequately occlude the blood vessels in the thinner sections. This embodiment also allows for variable adjustment of muscle tension such as where the muscle is strengthened or weakened more in one cross-sectional portion than another.

A muscle clip system, 6 mm to 8 mm in length should have two sutures whereas a shorter 3 to 4 mm clip, need only have a single suture connecting it to its opposing clip.

In another embodiment of this invention, a suture and needle are securely attached to a muscle clip as described above. In this embodiment, the muscle clip is attached to the muscle as described above and the muscle is severed at a point between the clip and the point of insertion. The muscle end attached to the eye is then cauterized by known procedures and the muscle clip is then sewn to the eye at a new location using the needle and suture attached thereto. This embodiment allows for hemostasis and provides for greater control by the surgeon over the operation.

Another embodiment of this invention utilizes a knot or swelling in the suture which would slide and temporarily hold the posterior and anterior clips a set distance from each other. A surgeon is then able to adjust the relative distance between the two clips at a later time when the patient is awake. This is currently done using the traditional surgical techniques and is termed adjustable suture strabismus surgery.

The Applicant is aware of the use in surgery of hemostatic clips such as those described in U.S. Pat. Nos. 3,326,216 and 3,363,628. The above mentioned patents teach the use of clips for strangling tubular members, particularly for the purpose of occluding blood vessels. These patents do not teach or anticipate the use of said hemostatic clips to facilitate muscle surgery.

BRIEF DESCRIPTION OF THE DRAWINGS

FIG. 3 is a top view of another embodiment of the present invention with a single suture connecting the clips such that the distance between the clips can be varied.

FIG. 7 is a top view of two suture versions of the invention such that the distance between the clips can be varied.

FIG. 5 is a top view in another embodiment of the present invention with a single suture with swellings and a slotted hole.

FIG. 6 is an enlarged section of a side view of the upper clip in FIG. 5 depicting the slotted hole.

FIG. 7a indicates the invented clips applied prior to incision. FIG. 7b is a top view of the invented muscle clip system following incision wherein the muscle relaxes back to a new position.

FIG. 8a indicates a top view with the invented muscle clips installed, prior to resection. FIG. 8b is a top view of the present invention with the muscle resected and the clips approximated.

DETAILED DESCRIPTION OF THE INVENTION

Figure 1:
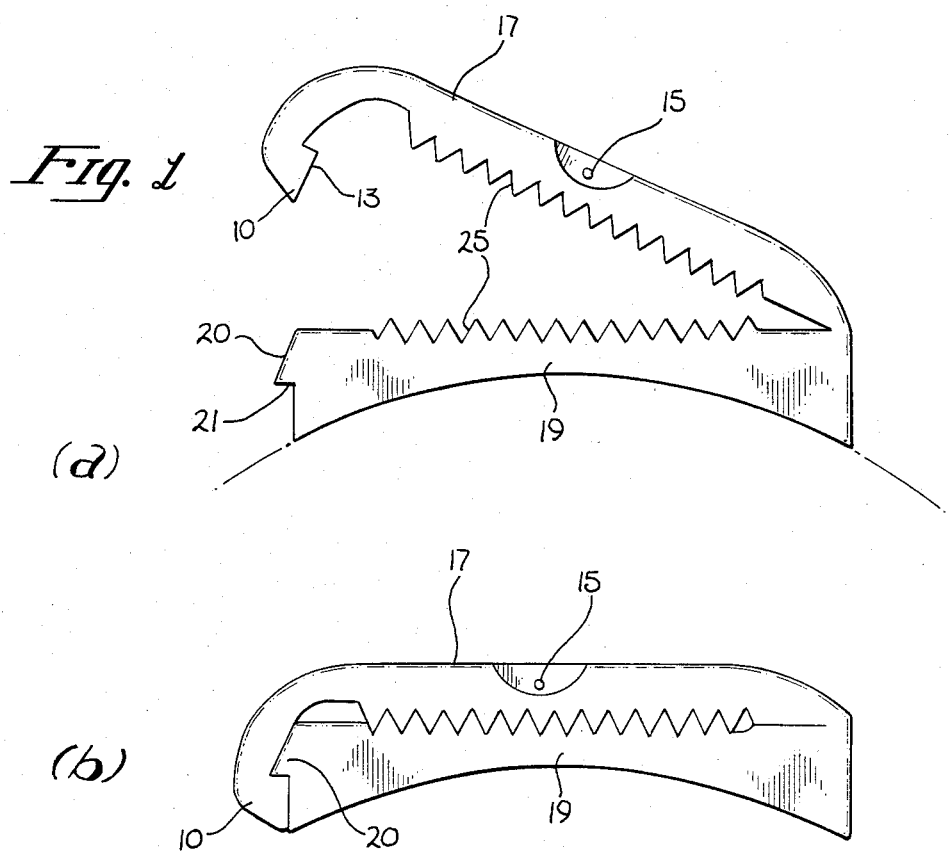
FIG. 1a is a side view of one embodiment of the invented clip in its open position.
FIG. 1b is a side view of the same clip in its closed position.

Illustrated in the drawings is an apparatus and method for absorbable, hemostasing, extra ocular muscle clips for needleless strabismus surgery. The body of the clip includes a hinge 12, upper jaws 17, lower jaws 19 and an outer 10 and inner 20 locking means. As generally illustrated in FIG. 1a, the body is preferably in the form of a pair of oppositely facing jaws formed from a single strip of absorbable material or inert plastic bent 180° along a line traversed to the longitudinal axis of the strip. Said clips may be made of an absorbable synthetic material (such as polydioxanone), silicone or other inert plastics which are or may be FDA approved for use in eye surgery. In the preferred embodiment, the hinge portion is a creased or weakened section at the center of the plastic strip, said plastic being resilient so as to allow angular mobility about the hinge point. The surfaces of said opposed jaws of said clips have teeth or serrations 25 which substantially mate when the clip is in the closed position (FIG. 1b). Said teeth are of such shape, dimensions, material and construction that the extra ocular muscle is tightly secured when the clip is in the closed and locked position without severing said muscle such that said clip can securely grasp when said muscle contracts with a force of 100 grams.

The locking means of the muscle clip is a resilient snap and locking means which allows the clip to remain in an open position so that it may be applied to the muscle. In the preferred embodiment, the outer portion of the locking means 10 bends outward away from the hinge 12 as it is forced against the inner portion 20 when the upper and lower jaws are squeezed together until the lip 13 is pushed past an indentation 21 such that the outer portion 10 snaps back and catches on the inner portion 20 of the locking means. The clip, when locked, may only be opened by the application of external forces not generally associated with the function of the extra ocular muscles.

Particularly with reference to the 3 mm to 4 mm clip, the locking means has at least one pointed member such that it can pierce through the extra ocular muscle enabling the locking means to fasten. In the alternative, an instrument can be used to separate the muscle between the inner and outer portions of the locking means allowing said portions to interlock. The locking means is spaced so that the jaws are sufficiently closed to clamp the blood vessels running through the muscle yet allow the jaws to close tightly onto the muscle as described above without severing the same.

The muscle clip may be applied using a sterile clamp or forceps type tool which can grasp the clip securely while allowing it to remain in an open position. Said tool can be positioned to slide the clip onto the extra ocular muscle and can squeeze the jaws together locking the clip.

Figure 2:
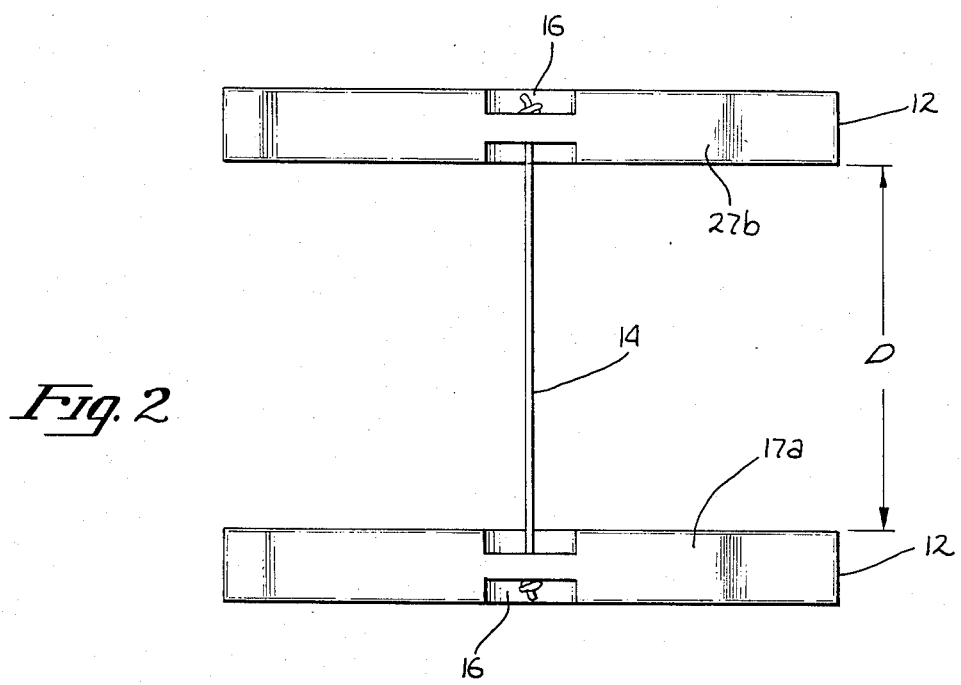
FIG. 2 is a top view of the muscle clip system wherein a single piece of suture material connecting the clips is of a predetermined length.

As illustrated in FIG. 2, the apparatus described herein may be in an embodiment wherein the muscle clips 27a and 27b may be connected together by suture material 14 such that there is a predetermined distance D between said clips. In this embodiment the suture material passes through a hole or slot 15 and is attached to the clips at 16.

FIG. 3 is an illustration of a muscle clip system wherein the distance between said clips can be varied by sliding muscle clip 27b along the suture material 14 and fixed by tying the suture using general surgical techniques. The muscle clips 27a and 27b are substantially similar to the clips described hereinabove. The suture material 14 is about 100 mm in the preferred embodiment to allow it to be easily tied.

In the muscle clip systems wherein the clips are 6 to 8 mm in length at least two sutures are required to prevent wobbling and uneven muscle action. In the 3 to 4 mm clip system wherein two clips applied transverse to the muscle and aligned with the locking means of said clips abutting to each other, only a single suture is needed for each clip. In the latter configuration, the aligned clips as a pair, have two sutures en toto to stabilize the clip system. In any clip system, more than two sutures connecting opposing clips could also be used. Referring to FIGS. 3 and 4, for example, FIG. 3 with its single suture connection depicts a 3 to 4 mm clip and would be approximately one half the length of the FIG. 4 clip with the two suture connecting means.

In FIG. 4, another embodiment of the present invention is illustrated wherein the suture material is attached securely to one of the clips 37a with two sutures emanating from two points 46a to 46b on said clip 37a. The sutures pass through holes or slots 47a and 47b in clip 37b opposite the points from which they emanate in the first clip so that the two sutures may be tied together, holding the clips in place at a distance D" from each other.

Figure 7A:
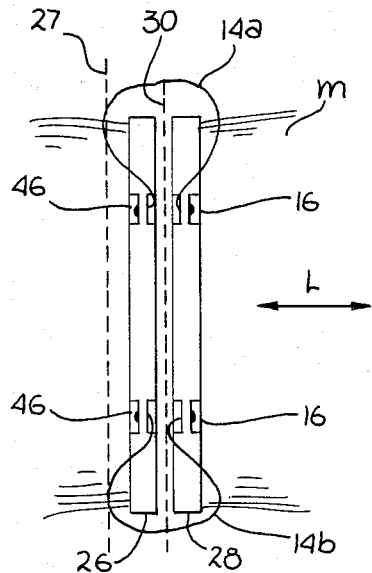
FIGS. 7a and 7b are top views of the present invention demonstrating the method whereby an extra ocular muscle is weakened.
Figure 7B:
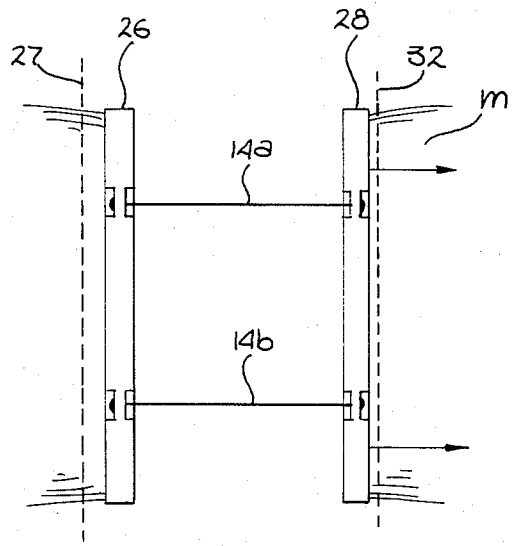

A better understanding of this invention can be found by reference to FIGS. 7a, 7b, 8a and 8b by examining the methods for using the muscle clips disclosed herein. FIGS. 7a and 7b demonstrate the operation of the muscle clip system depicted in FIG. 2, noting for reference, the eye and the extra ocular muscle attached thereto. This embodiment demonstrates the process of weakening said muscle.

One muscle clip 26 is attached to said muscle M perpendicular to its long axis L. Another clip 28 is attached to said muscle substantially parallel and adjacent to clip 26. The clips are connected by suture material 14a and 14b which is of a preselected length equal to the amount of recession or weakening desired. The anterior clip is attached close to the point of insertion 27. Using a cutting instrument, preferably a scissor, an incision at 30 is made between the anterior 26 and posterior 28 clips incising the muscle. The muscle then relaxes and the posterior clip falls back to a position more posterior as permitted by the preselected length of the suture material (FIG. 7b). The muscle will then reattach to the eye over about a two week period during which period tissue will grow due to the trauma and thereby secure the extra ocular muscle to the eye at the new point of insertion 32.

Figure 8A:
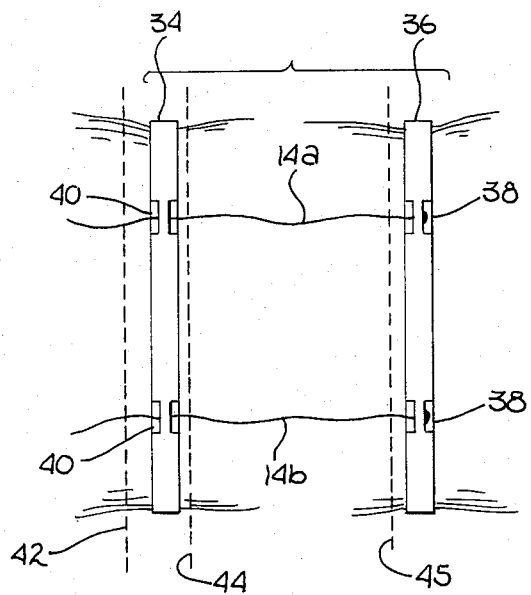
FIGS. 8a and 8b are top views of the muscle clip system whereby an extra ocular muscle is strengthened.
Figure 8B:
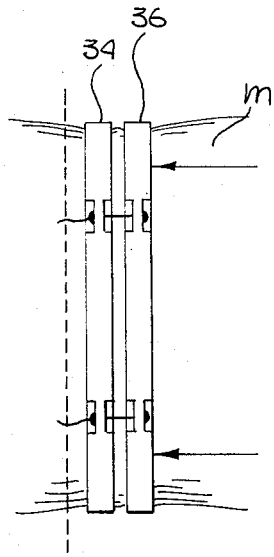

The achievement of muscle strengthening using the muscle clips described herein is illustrated in FIGS. 8a and 8b. The clips are again attached on the muscle in the same fashion as the surgical procedure described above except that the clips are applied to the muscle at points along said muscle such that the distance between said clips is equal to the amount of muscle to be resected, the distance D between said clips is measured as the internal distance between the anterior 34 and posterior 36 clips (FIG. 8a). Suture material is attached securely at points 38a and 38b to the posterior clip and passes through holes or slots 40a and 40b in the anterior clip, said suture material being at least 100 mm in length in the preferred embodiment. The anterior clip is, as in the embodiment described hereinbefore, attached near the insertion point 42 of the extra ocular muscle on the eye. Once the clamps are tightly attached grasping the muscle such that hemostasis is achieved, the muscle between the clips is resected, by cutting at points 44 and 46 and removed. The suture passing through the anterior clips is then pulled so that the posterior clips are adjacent the anterior clips and the sutures are then tied off so that the two ends of the muscle abut (FIG. 8b). A fibrous reaction occurs in which the muscle tissue associated with each clip fuses forming a single muscle. A tissue adhesive may also be used to secure the muscle.

The clips, which in the preferred embodiment are made from absorbable material, will be absorbed by the body such that no further surgery is needed to remove said clips following the initial implantation. If said material is polydioxanone, the absorption will occur over about 200 days. Said clips are prepackaged under sterile conditions such that easy removal and application under sterile conditions becomes a simple task.

In another embodiment of this invention, the muscle clips are 3 mm to 4 mm instead of 6 mm to 8 mm long with the same configuration of a hinged end, serrated or tooth jaws in the body portion and a locking means on the open end. In this embodiment each clip extends only half way across the muscle. The clips are attached from the transverse to the muscle in a straight line such that the respective hinges are facing away and the respective locking means facing towards each other. This embodiment has the advantage of a stronger grasp and security in case one clip malfunctions. It also has the advantage of the allowing the surgeon to adjust the tension of the muscle different amounts across the transverse axis.

In another embodiment of this invention illustrated in FIG. 5, the suture material has knots or swells 32 said suture being permanently affixed to one clip 57 at 16' and passing through a hole or loop 31 on the second clip 58. The distance d''' between said clips can be adjusted and then fixed by sliding the swelling or knot to a narrow portion 33 of the hole through which it cannot pass. In the preferred embodiment, said knots or swellings are spaced at 1 mm increments with the first knot closest to clip 57 located along the suture such that the clips are about 3 mm when said first knot is locked in said narrowed portion. This embodiment can be used for both the single and double suture systems. The narrowed portion 33 of the hole should be positioned towards the center of the muscle so that when the two sutures are tied together, the swelling 32 is held in the narrow portion 33 rather than the large hole 31. Narrowed slots such as 33 coming off both sides of the large hole would allow for this embodiment without requiring the manufacture of left hand and right hand clips. This method is useful for performing surgery wherein the surgeon may wish to readjust the position of the muscle when the patient is awake without the trauma of additional surgery. Once the proper positioning is determined, the suture material can then be permanently tied.

In another embodiment of the present invention, suture material with a needle attached at the end thereto, is attached to a single muscle clip. In this embodiment which can be used to weaken or strengthen a muscle, the muscle clip is applied to the extra ocular muscle to be recessed at a position posterior to the intended incision. Rather than clip the muscle with a second clip as described hereinabove, the needle is used to sew the muscle to its proper location. This embodiment allows for the hemostatic advantages of the clip but also allows the surgeon to perform traditional needle placement on the eye saving the step of needle placement in the muscle which has the potential dangers described above.

While the method and apparatus for hemostasing muscle clips for needleless surgery have been described herein, it will be apparent to those skilled in the art that the present invention may be used or modified for other purposes without departing from the spirit and scope of the invention.

Therefore, what I claim is:

1. An extraocular muscle clip system comprising:
   (i) a first and second elongated clip, each clip comprising:
      (a) a hinge means at one end;
      (b) a pair of oppositely facing jaws, said jaws being interconnected at said hinge means and having opposed faces surfaced with a muscle grabbing means, at least one of said jaws having an exterior surface adjacent the eye in use, said exterior surface being arcuately shaped to substantially conform to the curvature of the eye; and
      (c) an open end with a locking means whereby said jaws may be closed thereby securely clamping onto said muscle; and,
   (ii) a connecting means for connecting said first and second clips together.

2. The clip system of claim 1 wherein said muscle grabbing means comprises teeth disposed on oppositely facing surfaces of said jaws.

3. The clip system of claim 1 wherein said locking means further comprises:
   a resilient member, and
   a mating member, whereby said resilient member is diverged from its resting position as a result of force exerted by said mating member until said resilient member abuts a notch in said mating member so that it closes tightly and securely against said mating member.

4. The clip systems of claim 1 wherein said clip is approximately 3 millimeters in length.

5. The clip system of claim 1 wherein said clip is approximately 6 millimeters in length.

6. The clip system of claim 3 wherein said clip is formed from an absorbable, nontoxic, deformable, sterile material.

7. The clip system of claim 6 wherein said clip is formed of substances approved for eye surgery selected from the group consisting of inert plastic and silicone.

8. The clip of claim 1 wherein said exterior surface has a radius of curvature of approximately 12 millimeters.

9. The clip system of claim 1 wherein said connecting means comprises suture material.

10. The clip system of claim 9 wherein said suture material is attached to said clips such that said clips may be fixed in position at predetermined distances from each other.

11. The clip system of claim 10 wherein said suture material is fixed to said first clip and is adjustably attached to said second clip such that said second clip can be fixed in position at varying distances from said first clip.

12. The clip system of claim 11 wherein said suture material has enlarged portions disposed at predetermined intervals along its length and said second clip comprises a key-hole shaped slot having a large hole adjacent a narrow slot, whereby said enlarged portions of said suture material can pass through the large hole but cannot pass through the narrow slot.

13. In a system for extraocular muscle surgery, an improved muscle clip system comprising a first and second clip, each clip comprising a pair of jaws arranged laterally spaced apart in a substantially parallel relation, said jaws having teeth on the oppositely facing surfaces, an interconnecting edge acting as a hinge, and an open end having a locking means for securely closing said jaws together, one of said jaws having an exterior surface which in use is adjacent the eye, said exterior surface having a curvature approximating the curvature of said eye, wherein each of said first and second clips has at least one attachment site for attachment to a connecting means such that said first and second clips are connected together.

14. The system of claim 13 further comprising suture material connecting said first and second clip together at a preselected distance.

15. The system of claim 13 further comprising a suture material connecting said first and second clips together in a manner allowing said second clip to be secured at varying distances from said first clip along said suture.

16. The system of claim 13 wherein said clip is formed of nontoxic, deformable, absorbable, sterile material.

* * * * *

UNITED STATES PATENT AND TRADEMARK OFFICE
CERTIFICATE OF CORRECTION

PATENT NO. : 4,519,392

DATED : May 28, 1985

INVENTOR(S) : Lingua

It is certified that error appears in the above-identified patent and that said Letters Patent is hereby corrected as shown below:

| COLUMN | LINE | DESCRIPTION |
|---|---|---|
| 3 | 44 | Delete "Fig. 7" and insert --Fig. 4--. |
| 6 | 26 | Delete "of the allowing" and insert --of allowing--. |

Signed and Sealed this

Fourteenth Day of April, 1987

Attest:

DONALD J. QUIGG

Attesting Officer

Commissioner of Patents and Trademarks